(12) United States Patent
Efinger et al.

(10) Patent No.: US 9,044,184 B2
(45) Date of Patent: Jun. 2, 2015

(54) SPREADABLE MEDICAL INSTRUMENT FOR ENDOSCOPIC INTERVENTIONS

(75) Inventors: Andreas Efinger, Rietheim (DE); Rainer Hermle, Gosheim (DE)

(73) Assignee: KARL STORZ GMBH & CO. KG (DE)

( * ) Notice: Subject to any disclaimer, the term of this patent is extended or adjusted under 35 U.S.C. 154(b) by 431 days.

(21) Appl. No.: 11/232,300

(22) Filed: Sep. 20, 2005

(65) Prior Publication Data

US 2007/0060794 A1   Mar. 15, 2007

(30) Foreign Application Priority Data

Sep. 20, 2004  (DE) .......................... 10 2004 045 502

(51) Int. Cl.
*A61B 1/32* (2006.01)
*A61B 1/267* (2006.01)

(52) U.S. Cl.
CPC .. *A61B 1/267* (2013.01); *A61B 1/32* (2013.01)

(58) Field of Classification Search
CPC .................................. A61B 1/303; A61B 1/32
USPC .................................. 600/196, 220, 221–222
See application file for complete search history.

(56) References Cited

U.S. PATENT DOCUMENTS

| 672,239 | A | * | 4/1901 | Pilling | 600/220 |
|---|---|---|---|---|---|
| 1,150,749 | A | * | 8/1915 | Drosin | 600/226 |
| 3,332,414 | A | | 7/1967 | Gasper | 600/222 |
| 3,847,143 | A | | 11/1974 | Cotey et al. | 128/17 |
| 4,384,570 | A | | 5/1983 | Roberts | 128/4 |
| 5,092,314 | A | | 3/1992 | Zeitels | 128/10 |
| 5,460,165 | A | * | 10/1995 | Mayes | 600/186 |
| 5,499,964 | A | * | 3/1996 | Beck et al. | 600/220 |
| 5,938,591 | A | | 8/1999 | Minson | 600/191 |
| 6,416,467 | B1 | | 7/2002 | McMillin et al. | 600/224 |
| 6,494,828 | B1 | | 12/2002 | Berall | 600/190 |
| 2002/0165433 | A1 | | 11/2002 | Stihl | 600/196 |
| 2003/0176772 | A1 | * | 9/2003 | Yang | 600/220 |
| 2004/0002629 | A1 | * | 1/2004 | Branch et al. | 600/210 |

FOREIGN PATENT DOCUMENTS

| DE | 32 17 476 A1 | 12/1982 |
|---|---|---|
| DE | 19721138 C1 | 9/1998 |
| DE | 199 54 442 A1 | 6/2001 |
| WO | WO 98/01181 | 3/1998 |

OTHER PUBLICATIONS

European Search Report, Mar. 3, 2006, 9 pages.

\* cited by examiner

*Primary Examiner* — Cris L Rodriguez
*Assistant Examiner* — Hao D Mai
(74) *Attorney, Agent, or Firm* — St. Onge Steward Johnston & Reens LLC

(57) ABSTRACT

The invention relates to a spreadable medical instrument for endoscopic interventions having a base body, a handle positioned on the base body, and at least two spatula blades that are connected with the handle and can be displaced between a closed starting position and at least one working position parallel and/or at an angle to one another by means of an adjustment device, in such a way that the adjustment mechanism is positioned on the handle so that it is possible simultaneously to grip the handle and activate the adjustment mechanism with the same hand. To create a spreadable medical instrument that has the widest possible range of applications and is easy and safe to operate, it is proposed with the invention that the adjustment mechanism is configured as a continuous, adjustable screw-in mechanism.

10 Claims, 4 Drawing Sheets

SPREADABLE MEDICAL INSTRUMENT FOR ENDOSCOPIC INTERVENTIONS

CROSS REFERENCE TO RELATED APPLICATION

The present application claims priority of German patent application DE 10 2004 045 502.3 filed on Sep. 20, 2004.

FIELD OF THE INVENTION

The invention relates to a spreadable medical instrument for endoscopic interventions having a base body, a handle positioned on the base body, and at least two spatula blades that are connected to the handle and can be moved parallel and/or at an angle to one another by means of an adjustment mechanism between a closed starting position and at least one working position. The adjustment mechanism is positioned on the handle in such a way that it is possible to grip the handle and activate the adjustment mechanism simultaneously with the same hand.

BACKGROUND OF THE INVENTION

This type of spreadable instrument for endoscopic interventions is known in various embodiments. One preferred application is the configuration of such an instrument as a laryngoscope. Laryngoscopes are used particularly for direct instrumental inspection of the throat as well as for endolaryngeal surgical interventions. Owing to the adjustability of the spatula blades, it is possible to vary the free lumen that is formed by the spatula blades turned toward one another to form an essentially semicircular cross-section, in such a way that the laryngoscope is introduced in a closed starting position with a minimal lumen into the mouth and pharynx area of the intubated, anesthetized patient and that only afterward is the lumen enlarged by parallel and/or angular displacement of the spatula blades to one another so that appropriate medical instruments can be inserted into the laryngoscope.

Additional fields of application for such spreadable medical instruments include, in particular, neck surgery and the use of the mediastinoscope.

A generic spreadable medical instrument is described, for instance, in U.S. Pat. No. 5,938,591. This patent teaches a laryngoscope with two spatula blades which can be adjusted parallel and at angles to one another by means of a ratchet mechanism for each. These ratchet mechanisms are configured in such a way that, upon activation, they ratchet the blades in a pre-established ratchet position to one another. In addition to the protruding construction of the ratchet mechanism that stands far from the handle, this construction from the prior art has the disadvantage that the blades can be displaced with respect to one another only in the pre-established lock steps, which can in practice cause a position of the blades that is too narrow or else too wide for the current use.

Another instrument configured as a laryngoscope, for instance, is described in DE 199.54.442.A1. In this laryngoscope from prior art, the handle and the placement elements of the adjustment mechanism for adjusting the spatula blades are configured in such a way that the operator must use both hands for the purpose, which is not particularly advantageous in laryngoscopy since the laryngoscope, after positioning, must be securely fixed to the patient or the operating table.

However, for use in neck surgery, for instance, an endoscope with spatulas is inserted into an incision in the back of the neck and the spatulas then moves the tissue, stretching it apart until sufficient access to the operating area is provided.

For this operating technique, as well as for use as a mediastinoscope, it is essential that the operator has one hand free for operating additional medical instruments.

SUMMARY OF THE INVENTION

Consequently it is the object of the invention to design a spreadable medical instrument for endoscopic instruments in such a way that it has the widest possible range of applications and is simple to operate.

This object is met by the invention in that the adjustment mechanism is configured as a screw-in mechanism that is adjustable and continuous. The inventive design makes it possible for the first time to grip a spreadable medical instrument for endoscopic interventions with one hand and at the same time, with the same hand, to activate the continuous screw-in mechanism to displace the spatula blades, in such a way, for instance, that the operator can reach the screw-in mechanism and activate it using one or more fingers of the hand with which he grips the handle.

Because of this single-hand operation, the operator always keeps one hand free for operating an additional medical instrument. Therefore a spreadable medical instrument of this design also lends itself, in addition, to use as a laryngoscope in other endoscopic interventions and other applications.

The possible uses of the inventive instrument can be extended if the adjustment mechanism to displace the spatula blades includes a locking screw for parallel displacement of at least one of the blades, so that the blades can be either thrust forward or tipped independently of one another and continuously.

To hold the spatula blades in the selected position, it is further proposed with the invention that the locking screws are self-locking.

According to a practical embodiment of the invention it is proposed that the handle can be tipped with respect to the base body by means of the locking screw for tipping adjustment of at least one of the blades in addition or simultaneously. The handle's tippability gives the operator an additional possibility to move the medical instrument into a defined stable position.

To make it possible for the blades to be tippable with respect to one another even when the blades have not previously been thrust forward parallel to one another starting from the starting position adjacent to one another, it is proposed with the invention that at least one spatula blade includes a tapering on the proximal end configured in such a way that in the starting position with mutually adjacent, closed blades, a gap opens up between them toward the proximal end.

The tapering configured on at least one spatula blade ensures that the blades, while free from parallel slipping, can be tipped with respect to one another around a preselected angle, preferably 7 degrees.

To prevent, moreover, that, on approaching the closed position of the blades to one another, tissue can penetrate between the blades and possibly become squeezed there, it is proposed with the invention that the line of contact along which the two blades are adjacent to one another in the closed starting position, is configured in the area of the distal end in the shape of at least one step, which rises or sinks in the proximal direction. This stepped shape prevents, in approaching the closed position of the blades, the formation of a straight continuous gap between the blades, into which tissue could enter.

It is further proposed with the invention that the contact surfaces along which the two spatula blades are adjacent to one another in the closed starting position are configured as self-centering, so that any tilting and/or mutual overlapping or underlapping of the blades can be prevented, especially in the process of the blades' closing with respect to one another. According to a preferred embodiment of the invention, this self-centering is achieved in that the contact surfaces of the spatula blades, corresponding to one another, are configured at a diagonal angle to the center axis of the blades.

To allow simple and thorough cleansing of the inventive medical instrument, an endoscopic video camera that can be used with this instrument can be inserted as a replacement in the base body of the instrument.

Finally, it is proposed with the invention that one spatula blade has a guide sheath for inserting a camera lens. The use of this guide sheath, first, facilitates the insertion of the camera lens into the instrument and, second, permits an exact positioning of the lens while simultaneously protecting it from damage.

Further characteristics and advantages of the invention can be seen on the basis of the related drawings, which depict two embodiments of an inventive spreadable medical instrument for endoscopic interventions in merely schematic manner.

DETAILED DESCRIPTION OF THE INVENTION

The spreadable medical instrument depicted in the illustrations consists essentially of a base body 2 equipped with a handle 1 and, connected with the handle 1, two spatula blades 3 and 4 which can be displaced with respect to one another by means of an adjustment mechanism 5.

A medical instrument of this type can be used, for instance, as a laryngoscope or mediastinoscope as well as an instrument for endoscopic neck surgery. A defining characteristic of these spreadable medical instruments is that the spatula blades 3, 4 can be moved between a closed starting position and at least one spreaded working position in which the spatula blades 3, 4 are displaced parallel and/or at an angle to one another.

Figure 1:
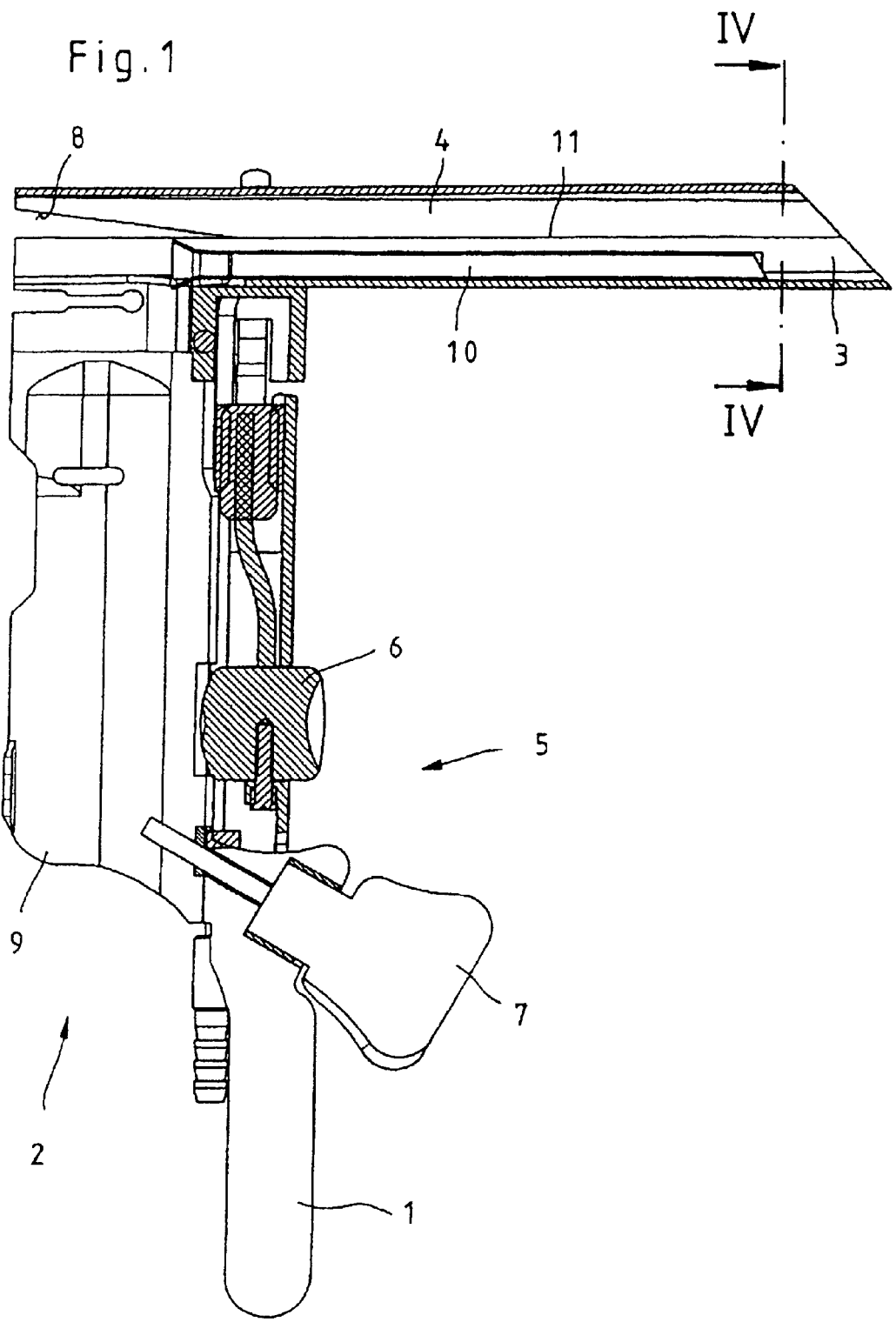
FIG. 1 shows a partial cutout side view of a first embodiment of an inventive spreadable medical instrument in the closed position.

The illustration in FIG. 1 shows the instrument in the closed starting position, in which the spatula blades 3, 4 are firmly adjacent to one another to enable the spatula part of the instrument with a minimal lumen to be inserted into the operating area, for instance into the mouth and throat area during use of a laryngoscope, and to be removed again from it. The remaining lumen is sufficient for determining the position of the instrument in the operating area by means of an affixed or inserted lighting device.

Because the spatula blades 3 and 4 are movable, it is possible that the free lumen formed by the blades 3, 4 being turned toward one another and configured in an essentially half-circular cross-section can be varied in such a way that, proceeding from the closed starting position, this lumen is enlarged subsequently by parallel and/or angled displacement of the blades 3, 4 to one another in such a way that appropriate medical instruments can be inserted into the spreaded blades 3, 4.

Figure 2:
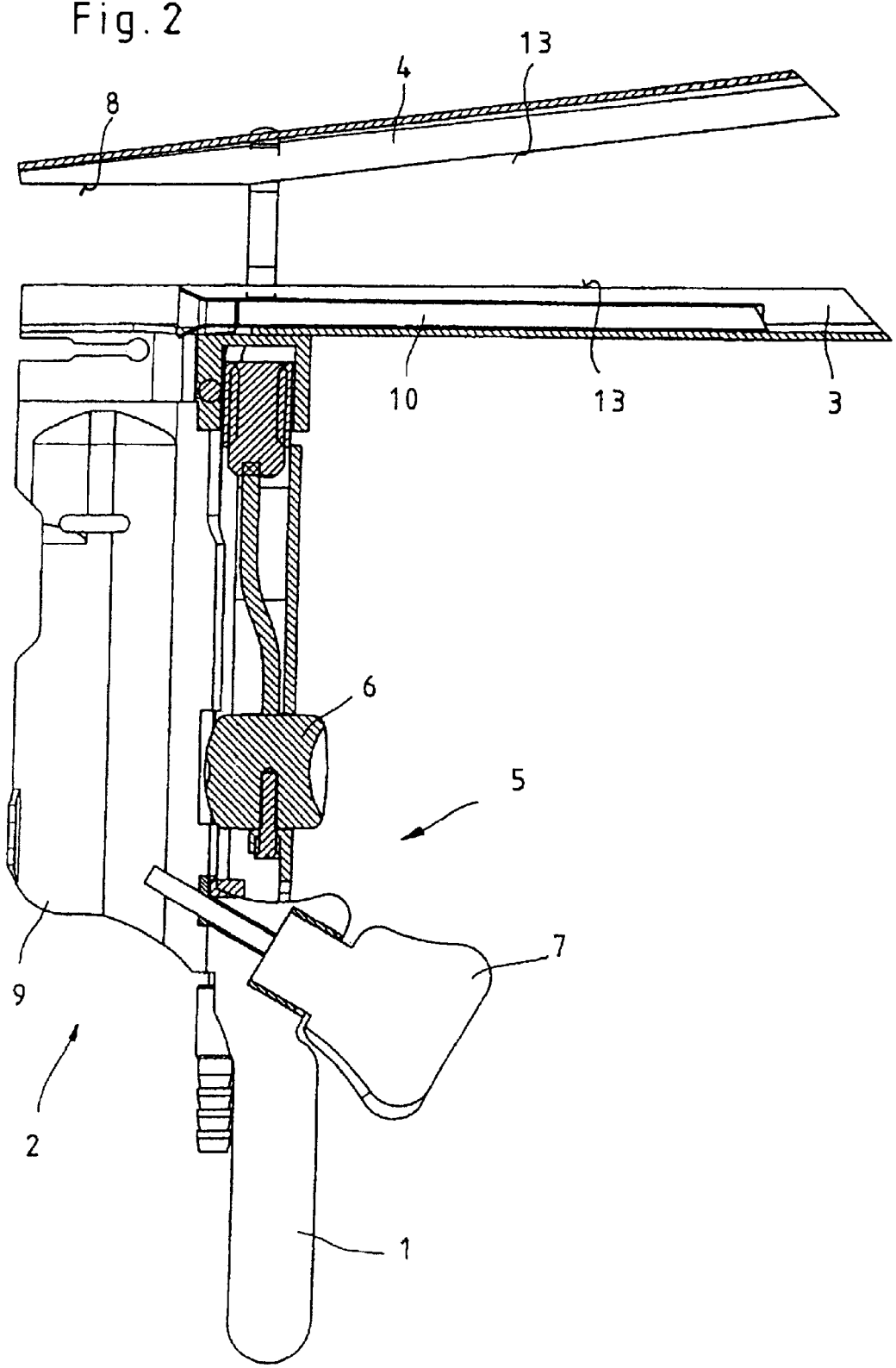
FIG. 2 shows a sectional view according to FIG. 1, but with the medical instrument in an open working position.
Figure 3:
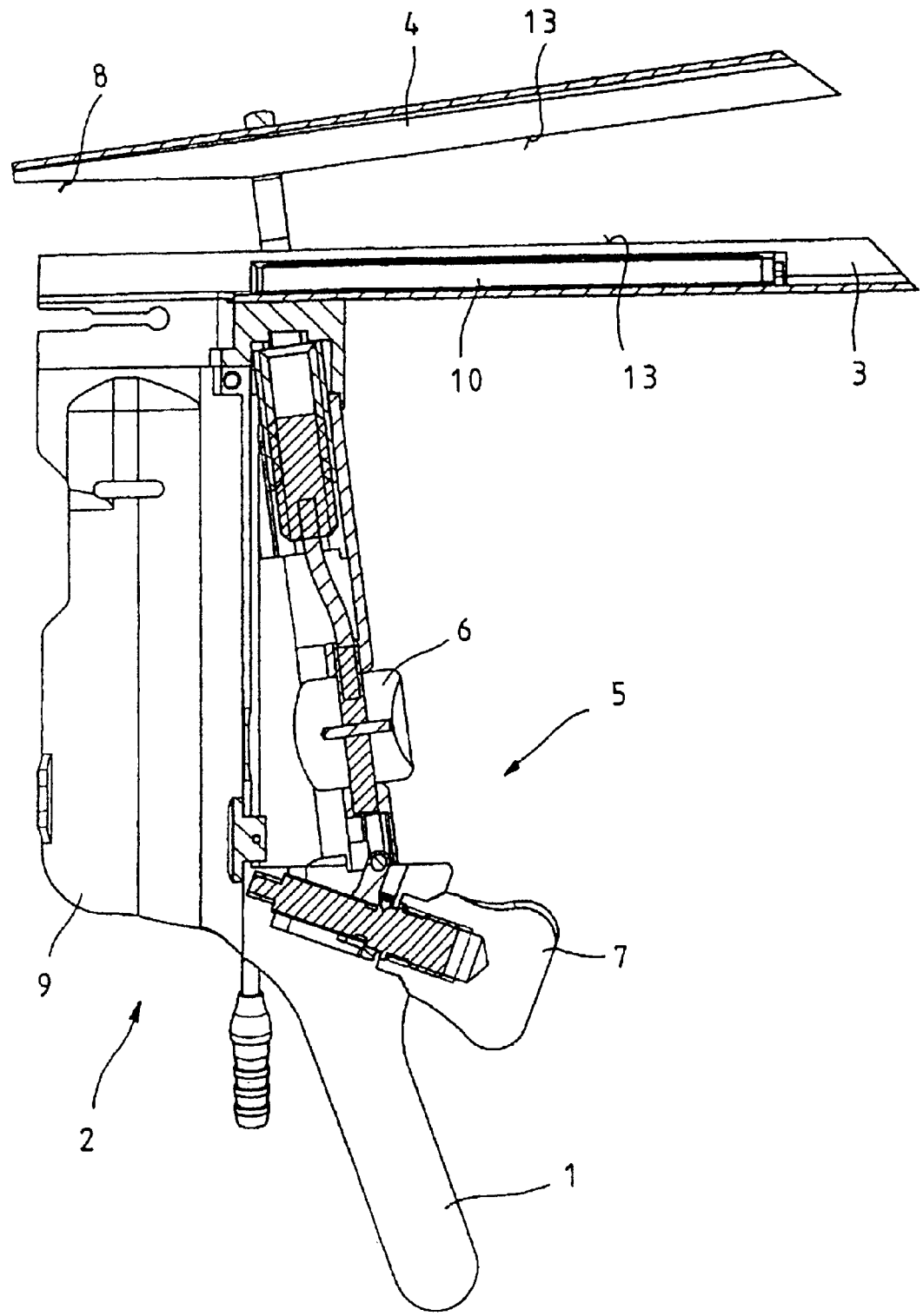
FIG. 3 shows a sectional view according to FIG. 2, but showing the medical instrument in addition with the handle tipped.

As can be seen from FIGS. 1 to 3, the adjustment mechanism 5 for displacing the spatula blades 3, 4 in the illustrated embodiment consists of two separate, continuous displaceable locking screws 6 and 7, in such manner that activating the locking screw 6 causes parallel moving of the blade 4 with respect to blade 3 and blade 4 can be tipped with respect to blade 3 by means of the locking screw 7, as can be seen from FIGS. 2 and 3. FIG. 3 also shows that in addition the handle 1 can be configured so that it can tip with respect to the ground body 2 by means of the locking screw 7 in order to ensure the operator at all times an appropriate, safe working posture.

It is also possible, of course, to combine the locking screws 6 and 7 in a single locking screw by which, for example, both displacement possibilities, that is, parallel motion and tipping, can be carried out when required and without successive steps through various switching directions.

As can further be seen from FIGS. 1 to 3, the locking screws 6 and 7 of the adjustment mechanism 5 are positioned on the handle 1 in such a way that it is possible to grip the handle 1 and to activate the adjustment mechanism 5 simultaneously with the same hand, in such manner that, for instance, the operator can reach and activate the adjustment mechanism 5 using one or more fingers of the hand with which he grasps the handle 1.

To enable the spatula blades to be tipped even when the blades 3, 4, from the starting position adjacent to one another, have not been previously pushed together parallel, blade 4 in the illustrated embodiment has on its proximal end a tapering 8 configured in such a way that in the closed starting position with the blades 3, 4 adjacent to one another, an open gap is formed as far as the proximal end. Of course it is also possible to configure the tapering 8 only on blade 3 or on both blades 3, 4.

The tapering 8, which also forms a stop for the maximum tipping angle, can be selected and set, before the use of the instrument, depending on the corresponding choice of spatula blades 3, 4 corresponding to the respective application. In laryngoscopy, for instance, this angle is preferably 7 degrees.

The base body 2 of the medical instrument consists essentially of a camera compartment 9 that can be opened and closed again and serves as a space for inserting a replaceable endoscopic video camera. Contrary to the state-of-the-art permanently built-in video camera, a replaceable model has the advantage that the entire instrument can be easily and completely cleaned, for instance by autoclaving. For insertion of the camera lens, a guide sheath 10 is positioned on the interior of spatula blade 3. Use of this guide sheath 10, first, facilitates insertion of the camera lens into the instrument and, second, allows exact positioning of the lens while serving as protection from damage.

Figure 5:
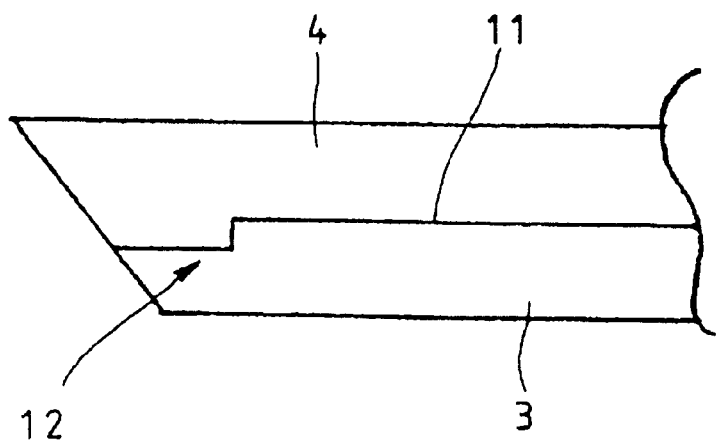
FIG. 5 shows a detail schematic side view of a second embodiment showing the design of the spatula blades.

To prevent, on approaching the closed position of the spatula blades 3, 4, tissue from penetrating between the blades 3, 4 and possibly become caught there, the contact line 11 along which the two blade 3, 4 are adjacent to one another in the closed starting position, is configured in the shape of at least one step 12, as can be seen in the embodiment shown in FIG. 5. This step shape prevents, on approaching the closed position of the blades 3, 4, the formation of a straight-line gap extending between the blades 3, 4 into which tissue could penetrate.

Figure 4:
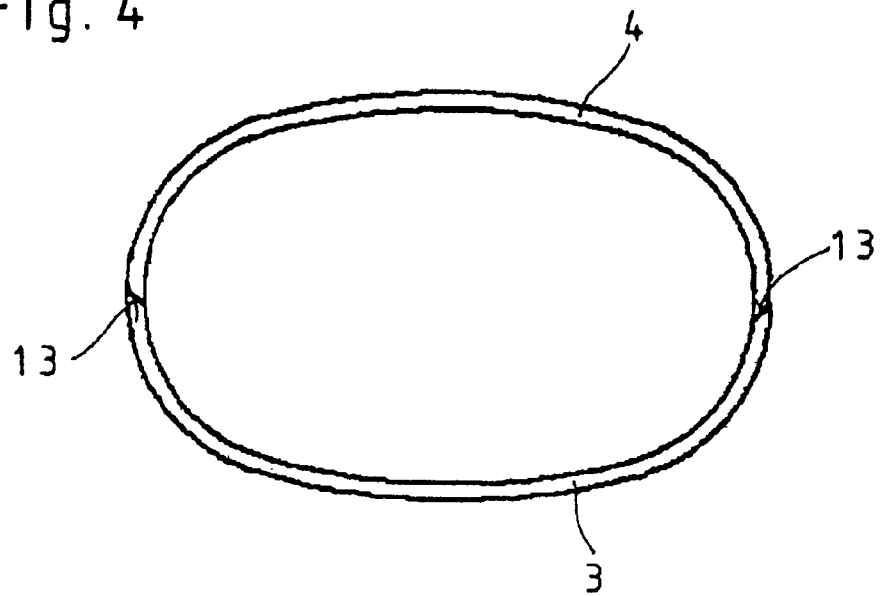
FIG. 4 shows an enlarged sectional view along the line IV-IV according to FIG. 2.

Finally, FIG. 4 shows a particular embodiment of the contact surfaces 13, along which the two spatula blades 3, 4 are adjacent to one another in the closed starting position. As can be seen from the illustration, the contact surfaces 13 of the blades 3, 4 are configured correspondingly to one another at an angle to the center axis of the blades 3, 4. This angular configuration causes self-centering of the blades 3, 4 in the closed position, so that tipping, rotating, and/or mutual overlapping or underlapping of the spatula blades 3, 4 is prevented.

A spreadable medical instrument configured in this manner is distinguished in that it can be applied in a variety of ways and is simple to operate because of the possibility of one-hand operation.

What is claimed is:

1. A spreadable medical instrument for endoscopic interventions comprising:
    a base body,
    a handle positioned on the base body,
    two spatula blades connected to the handle; and
    an adjustment mechanism for displacing said two spatula blades from a starting closed position wherein the two spatula blades are adjacent to each other into a working position wherein the two spatula blades are spreaded from each other by parallel and/or tipping displacement;
    wherein the two spatula blades have a proximal end positioned close to the handle, wherein at least one of the two spatula blades has a tapering at the proximal end, the tapering defines a gap at the proximal end between the two spatula blades in the starting closed position, and the gap opens up toward the proximal end;
    wherein the adjustment mechanism includes a first adjusting screw for parallel displacement of at least one of the two spatula blades into a parallel working position and a second adjusting screw for tipping displacement of at least one of the two spatula blades into an angled working position, the first adjusting screw and the second adjusting screw being positioned close to one another on the handle to allow simultaneous gripping of the handle and rotation of one or both of the first and second adjusting screws with one hand only,
    wherein the adjustment mechanism is a continuously adjustable screw-in mechanism for displacing the two spatula blades into a positions between the starting closed position and the working position, wherein rotation of one or both of the first and second adjusting screws directly displaces and fixes at least one of the two spatula blades into the working position, and
    wherein the first and second adjusting screws are self-locking.

2. The spreadable medical instrument according to claim 1, wherein the handle can be tipped with respect to the base body.

3. The spreadable medical instrument according to claim 2, wherein the handle can be tipped with respect to the base body by means of the second adjusting screw.

4. The spreadable medical instrument according to claim 1, wherein the two spatula blades can be tipped toward one another at a pre-selected angle, by means of the tapering without previously spreading the two spatula blades by parallel displacement.

5. The spreadable medical instrument according to claim 1, wherein the two spatula blades have a distal end positioned far away from the handle,
    wherein a contact line along which the two spatula blades are adjacent to one another in the starting closed position is configured to have a first straight line and a second straight line, wherein the second straight line and the first straight line are parallel to each other, wherein one end of the first straight line is connected to one end of the second straight line by at least one step near the distal end.

6. The spreadable medical instrument according to laim 1, wherein contact surfaces along which the two spatula blades are adjacent to one another in the starting closed position are configured to be self-centering.

7. The spreadable medical instrument according to claim 6, wherein the contact surfaces of the two spatula blades corresponding to one another are configured at an angle to a center axis of the spatula blades.

8. The spreadable medical instrument according to claim 1, wherein an endoscopic video camera can be exchangably inserted into the base body.

9. The spreadable medical instrument according to claim 8, wherein one of the two spatula blades includes a guide sheath positioned on an interior thereof for insertion of a video camera lens.

10. The spreadable medical instrument according to claim 4, wherein the pre-selected angle is 7 degrees.

* * * * *